United States Patent [19]

Stenzel

[11] Patent Number: 4,582,834

[45] Date of Patent: Apr. 15, 1986

[54] SUBSTITUTED PHENYL-2-(1H)-PYRIMIDINONES USEFUL FOR TREATING CARDIAC INSUFFICIENCY IN A WARM-BLOODED ORGANISM

[75] Inventor: Wolfgang Stenzel, Reinbek, Fed. Rep. of Germany

[73] Assignee: Beiersdorf Aktiengesellschaft, Hamburg, Fed. Rep. of Germany

[21] Appl. No.: 601,182

[22] Filed: Apr. 17, 1984

[30] Foreign Application Priority Data

Apr. 30, 1983 [DE] Fed. Rep. of Germany ....... 3315797

[51] Int. Cl.⁴ ................. A61K 31/505; C07D 239/02
[52] U.S. Cl. ..................................... 514/274; 544/315
[58] Field of Search ................. 544/315; 424/251; 514/274

[56] References Cited

U.S. PATENT DOCUMENTS 3,829,422  8/1974  Hardtmann ........................ 544/315

OTHER PUBLICATIONS

Hubert–Habart et al., Chim. Therapeutique 1968, 4, 280–288.
Hubert–Habart et al., Chimie Therapeutique, 1973, 3, 314–318.
Takagi et al., Chim. Therapeutique, 1970, 5, 264–269.
Wolfe et al., Chem. Abst. 85-16560r.
Murray et al., J. Org. Chem. vol. 99, 1974, pp. 595–600.
Wolfe et al., J. Het. Chem. 13, (1976), pp. 383–385.

Takaji et al., Chem. Pharm. Bull. vol. 23, pp. 2427–2431, (1975).
Hubert–Habart et al., Chem. Abst. vol. 70-37765z.
Hubert–Habart et al., Chem. Abst. vol. 79-105183w.
Murray et al., Chem. Abst. vol. 80-95869d.
Takagi et al., Chem. Abst. vol. 84-30999j.

*Primary Examiner*—Donald G. Daus
*Assistant Examiner*—Cecilia Shen
*Attorney, Agent, or Firm*—Sprung Horn Kramer & Woods

[57] ABSTRACT

New substituted phenyl-2-(1H)-pyrimidinones of the general formula I

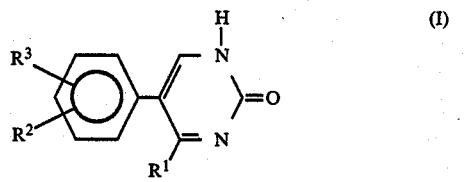

in which $R^1$ denotes an alkyl group having 1 to 4 carbon atoms, and $R^2$ and $R^3$, which can be identical or different, each denote hydrogen, halogen, cyano, a trifluoromethyl group, a hydroxyl group or an alkoxy group having 1 to 4 carbon atoms, it being possible for each alkyl moiety to be straight-chain or branched, and their tautomeric forms and their acid addition salts and N-oxides have a positive inotropic effect and can thus be used as medicaments for the treatment of cardiac insufficiency.

5 Claims, No Drawings

SUBSTITUTED PHENYL-2-(1H)-PYRIMIDINONES USEFUL FOR TREATING CARDIAC INSUFFICIENCY IN A WARM-BLOODED ORGANISM

The invention relates to new substituted phenyl-2-(1H)-pyrimidinones of the formula I

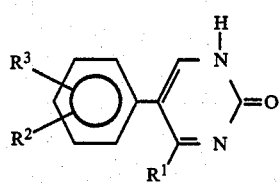

in which $R^1$ denotes an alkyl group having 1 to 4 carbon atoms, and $R^2$ and $R^3$, which can be identical or different, each denote hydrogen, halogen, cyano, a trifluoromethyl group, a hydroxyl group or an alkoxy group having 1 to 4 carbon atoms, it being possible for each alkyl moiety to be straight-chain or branched, and to their tautomeric forms and their acid addition salts and N-oxides, to a process for their preparation and to their use in pharmaceutical products.

For simplicity, the compounds according to the invention are defined in only one tautomeric form represented by formula I. However, the invention extends to all tautomeric forms of the compounds.

Although pharmaceutically tolerated salts of the new compounds of the formula I and their tautomeric forms and N-oxides are preferred, all acid addition salts lie within the scope of the invention. All acid addition salts are valuable for the preparation of the bases, even when the specific salt is only required as an intermediate, such as, for example, when the salt is formed only for the purposes of purification or identification, or if it is used as an intermediate for the preparation of a pharmaceutically tolerated salt, for example by ion exchange procedures.

The invention also relates to the N-oxides of the compounds of the general formula I. They can be obtained by known preparation processes (H. S. Mosher et al., Org. Synth., Coll. Vol. IV, 828, 1963).

The alkyl groups and the alkyl moieties in the alkoxy groups can be straight-chain or branched according to the invention.

The methyl and ethyl groups are particularly preferred alkyl groups $R^1$.

The radicals $R^2$ and $R^3$ are preferably located in the 3-position and/or 4-position of the phenyl radical.

Halogen is preferably fluorine or chlorine.

Methoxy and ethoxy groups are preferred alkoxy groups.

The following compounds of the general formula I, their N-oxides and their salts are particularly preferred:
5-(3-hydroxyphenyl)-4-methyl-2-(1H)-pyrimidinone hydrobromide,
5-(3-hydroxyphenyl)-4-ethyl-2-(1H)-pyrimidinone hydrobromide,
5-(3-methoxyphenyl)-4-methyl-2-(1H)-pyrimidinone,
5-(3-chlorophenyl)-4-methyl-2-(1H)-pyrimidinone,
5-(4-hydroxyphenyl)-4-methyl-2-(1H)-pyrimidinone hydrobromide,
5-(4-hydroxyphenyl)-4-ethyl-2-(1H)-pyrimidinone hydrobromide,
5-(4-methoxyphenyl)-4-methyl-2-(1H)-pyrimidinone and
5-(4-chlorophenyl)-4-methyl-2-(1H)-pyrimidinone.

The substances according to the invention, their physiologically tolerated acid addition salts and N-oxides have valuable pharmacological properties, in particular a positive inotropic effect, and are thus suitable for the treatment of cardiac insufficiency.

The compounds of the present invention can be administered orally or parenterally to humans at a dosage of 10–1,200 mg, preferably 100–800 mg, particularly preferably 300–600 mg, per day, in particular in divided doses, for example thrice daily. This dosage applies particularly to the treatment of cardiac insufficiency.

The positive inotropic effect of the compounds according to the invention has been determined on the papillary muscle of guinea pigs (Naunyn-Schmiedeberg's, Arch. Pharmacol. 304, 37 (1978)). The concentration of the substance in the organ bath was $3 \times 10^{-4}$ mol/l in each case. The maximum percentage increase in the amplitude of contractions was determined on three papillary muscles in each case, and was at least 50%.

According to the invention, pharmaceutical compositions which contain a compound of the formula I and its N-oxides or its pharmaceutically tolerated salts, together with a pharmaceutically tolerated diluent or vehicle, are produced.

The compounds according to the invention can be mixed with customary pharmaceutically tolerated diluents or vehicles and, where appropriate, with other auxiliaries, and can be administered, for example, orally or parenterally. They can be administered orally in the form of tablets, coated tablets, syrups, suspensions and liquids, or parenterally in the form of solutions or suspensions. Products for oral administration can contain one or more additives, such as sweeteners, flavourings, colorants and preservatives. Tablets can contain the active compound mixed with customary pharmaceutically tolerated auxiliaries, for example inert diluents, such as calcium carbonate, sodium carbonate, lactose and talc, granulating agents and agents which promote the disintegration of the tablets on oral administration, such as starch or alginic acid, binders, such as starch or gelatin, and lubricants, such as magnesium stearate, stearic acid and talc.

Examples of suitable vehicles are lactose, gelatin, maize starch, stearic acid, ethanol, propylene glycol, ethers of tetrahydrofuryl alcohol, and water.

The tablets can be coated by known procedures in order to retard the disintegration and absorption in the gastrointestinal tract, and by this means the activity of the active compound can extend over a prolonged period. Likewise, in the suspensions, the active compound can be mixed with auxiliaries which are customary for the preparation of compositions of these types, for example suspending agents, such as methylcellulose, tragacanth or sodium alginate, wetting agents, such as lecithin, polyethylene stearate and polyoxyethylene sorbitan monooleate, and preservatives, such as ethyl parahydroxybenzoate. Capsules can contain the active compound as the only constituent or mixed with a solid diluent, such as calcium carbonate, calcium phosphate or kaolin. The injectable products are likewise formulated in a manner known per se. The pharmaceutical products can contain the active compound in an amount of from 0.1 to 90%, in particular 1 to 90%, the remainder being a vehicle or additive. Having regard to the preparation and administration, solid products, such as tablets and capsules, are preferred. The products preferably contain the active compound in an amount of 100 mg.

The new compounds of the general formula I can be prepared by reacting compounds of the formula II

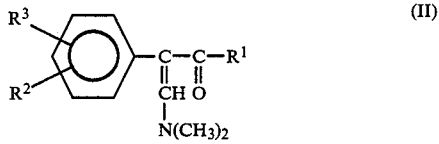

in which R¹ denotes an alkyl group having 1 to 4 carbon atoms, and R² and R³, which can be identical or different, each denote hydrogen, halogen, cyano, a trifluoromethyl group, a hydroxyl group or an alkoxy group having 1 to 4 carbon atoms, it being possible for each alkyl moiety to be straight-chain or branched, with urea.

The reaction of the compounds of the formula II with urea is preferably carried out by heating in a suitable solvent, such as methanol, ethanol or dimethylformamide, in the presence of a basic condensing agent, preferably an alkali metal alcoholate, such as sodium methylate. Other suitable solvents are toluene, dioxane, acetonitrile or tetrahydrofuran. The reaction temperatures are between 65° and 150° C. The reaction times vary, according to the reaction conditions chosen, between 8 and 48 hours. The optimum reaction times are advantageously determined by thin-layer chromatography on silica gel.

Compounds of the formula I in which at least one of R² and R³ denotes an alkoxy group can be converted by ether cleavage into the corresponding hydroxy derivatives according to the invention. For the ether cleavage, hydrobromic acid, or other reagents suitable for this reaction, such as boron tribromide or trimethylsilyl iodide, is preferably used.

The compounds of the formula II can be prepared from aryl ketones of the formula III

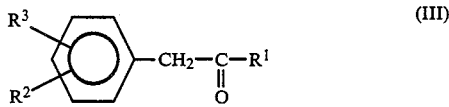

in which R¹ denotes an alkyl group having 1 to 4 carbon atoms, and R² and R³, which can be identical or different, each denote hydrogen, halogen, cyano, a trifluoromethyl group, a hydroxyl group or an alkoxy group having 1 to 4 carbon atoms, it being possible for each alkyl moiety to be straight-chain or branched, by reaction with dimethylformamide dimethyl acetal.

The reactions can be carried out in a solvent such as dimethylformamide or without solvent, at temperatures between 50° C. and the boiling point of the reaction mixture, preferably between 70° and 100° C.

If the reaction is carried out without a solvent but with an excess of dimethylformamide dimethyl acetal at 70° to 100° C., then the reaction times are between one and eight hours.

The starting compounds used in the process are known or can be prepared by known methods.

The compounds of the general formula I can be isolated from the reaction mixtures either as the bases or in the form of their salts. As bases, they can be converted by known processes into salts using suitable inorganic or organic acids.

A resulting basic compound can be converted into a corresponding acid addition salt, for example by reacting it with an inorganic or organic acid, such as a therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulphuric, phosphoric, nitric or perchloric acid, or organic acids, e.g. carboxylic or sulphonic acids, such as formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, aminosalicylic, embonic, nicotinic, methanesulphonic, ethanesulphonic, hydroxy-ethanesulphonic, ethylenesulphonic, benzenesulphonic, halogenobenzenesulphonic, toluenesulphonic, naphthalenesulphonic and sulphanilic acid; methionine, tryptophan, lysine and arginine.

Salts of the abovementioned acids or other salts, for example the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Physiologically tolerated salts are preferred. Examples of inorganic acids suitable for these are hydrogen halide acids, for example hydrochloric acid, or sulphuric acid, and examples of suitable organic acids are fumaric acid, maleic acid, citric acid and tartaric acid. For their preparation, the alcoholic solution of a suitable acid is added to the hot alkaline solution of the base, and the salt is obtained after addition of ether.

The examples which follow serve to illustrate the invention:

EXAMPLE 1

5-(4-Hydroxyphenyl)-4-methyl-2-(1H)-pyrimidinone hydrobromide 1.5 g of 5-(4-methoxyphenyl)-4-methyl-2-(1H)-pyrimidinone are heated with 12.5 ml of 47% hydrobromic acid at 100° C. for 24 hours. The mixture is then cooled to 0° C., and the product which has crystallised out is filtered off with suction and washed with cold ethanol. 1.3 g of 5-(4-hydroxyphenyl)-4-methyl-2-(1H)-pyrimidinone hydrobromide are obtained. Melting point above 300° C.

EXAMPLE 2

5-(4-Methoxyphenyl)-4-methyl-2-(1H)-pyrimidinone 35 g of 3-(4-methoxyphenyl)-2-propanone and 70 ml of dimethylformamide dimethyl acetal are heated at 70° C. for 3 hours. The reaction mixture is then evaporated to dryness in vacuo, and the residue is induced to crystallise with petroleum ether and the crystals are filtered off with suction. 43 g of 4-dimethylamino-3-(4-methoxyphenyl)-3-buten-2-one are obtained. Melting point 51° C.

24.4 g of urea and 120 ml of a 25 percent ethanolic solution of sodium ethylate are added to a solution of 40.0 g of 4-dimethylamino-3-(4-methoxyphenyl)-3-buten-2-one in 120 ml of ethanol. The mixture is heated at the reflux temperature for 8 hours, then cooled to 0° C., and the reaction product is filtered off with suction and washed with cold ethanol. The residue is dissolved in water and, while cooling in ice, is neutralised with dilute hydrochloric acid. The precipitated product is filtered off with suction, washed with water and dried. 19.5 g of 5-(4-methoxyphenyl)-4-methyl-2-(1H)-pyrimidinone are obtained. Melting point 210° C.

3.5 g of 5-(4-methoxyphenyl)-4-methyl-2-(1H)-pyrimidinone are dissolved in methanol, the solution is acidified with ethereal hydrochloric acid (pH 2–3), and ether is added to incipient opalescence. The solution is cooled and the crystals are filtered off with suction. After drying, 3.3 g of 5-(4-methoxyphenyl)-4-methyl-2-(1H)-pyrimidinone hydrochloride are obtained. Melting point 265° C. (decomposition).

EXAMPLE 3

5-(2-Hydroxyphenyl)-4-methyl-2-(1H)-pyrimidinone hydrochloride 100 ml of 40 percent hydrobromic acid in glacial acetic acid are added to 10.0 g of 5-(2-methoxyphenyl)-4-methyl-2-(1H)-pyrimidinone, and the mixture is heated under reflux for 48 hours. It is then evaporated, and the residue is triturated with ether and filtered off with suction. The crude product is dissolved in 100 ml of water, and the solution is decolourised with active charcoal and neutralised with dilute sodium hydroxide solution. The precipitate is filtered off with suction, dried and dissolved in methanol, and the solution is adjusted to pH 2 with ethereal hydrochloric acid, and ether is added to incipient opalescence. The solution is then cooled, and the residue is filtered off with suction and recrystallised from ethanol. 2.5 g of 5-(2-hydroxyphenyl)-4-methyl-2-(1H)-pyrimidinone hydrochloride are obtained. Melting point 241°–243° C. (decomposition).

Preparation of tablets and capsules

Tablets and capsules which contain the constituents indicated below are prepared by known procedures. These are suitable for the treatment of cardiac insufficiency in dosage amounts of one tablet or capsule thrice daily in each case.

| Constituents | Weight (mg) Tablet | Weight (mg) Capsule |
| --- | --- | --- |
| 5-(4-Hydroxyphenyl)-4-methyl-2-(1H)—pyrimidinone hydrobromide | 100 | 100 |
| Tragacanth | 10 | — |
| Lactose | 247.5 | 300 |
| Maize starch | 25 | — |
| Talc | 15 | — |
| Magnesium stearate | 2.5 | — |

The compounds according to the invention which are indicated in the table below were obtained as indicated:

| Example No. | $R^1$ | $R^2$ | $R^3$ | Melting point °C. | Salt/Base | Prepared in analogy to Example No. |
| --- | --- | --- | --- | --- | --- | --- |
| 4 | $C_2H_5$ | 4-$OCH_3$ | H | 155 | Base | 2 |
| 5 | $C_2H_5$ | 4-OH | H | 302 (decomp.) | Hydrobromide | 1 |
| 6 | $CH_3$ | 2-$OCH_3$ | H | 225 | Hydrochloride | 2 |
| 7 | $CH_3$ | 3-$OCH_3$ | H | 253 | Hydrochloride | 2 |
| 8 | $CH_3$ | 3-OH | H | 287 (decomp.) | Hydrobromide | 3 |
| 9 | $CH_3$ | 3-$OCH_3$ | 4-$OCH_3$ | 250 | Hydrochloride | 2 |
| 10 | $CH_3$ | 3-OH | 4-OH | 289 | Hydrobromide | 1 |
| 11 | $CH_3$ | 2-$OCH_3$ | 5-$OCH_3$ | 170 | Base | 2 |
| 12 | $CH_3$ | 2-OH | 5-OH | 289 | Hydrobromide | 3 |
| 13 | $CH_3$ | 4-$OCH(CH_3)_2$ | H | 256 | Hydrochloride | 2 |
| 14 | $CH_3$ | H | H | 260 (decomp.) | Hydrochloride | 2 |
| 15 | $CH_3$ | 2-Cl | 4-Cl | 230 | Base | 2 |
| 16 | $CH_3$ | 4-Cl | H | 203 | Base | 2 |
| 17 | $CH_3$ | 4-$CH_3$ | H | 246 | Base | 2 |
| 18 | $CH_3$ | 4-$CH(CH_3)_2$ | H | 203 | Base | 2 |
| 19 | $CH_3$ | 2-$OCH_3$ | 4-$OCH_3$ | 225 (decomp.) | Hydrochloride | 2 |
| 20 | $CH_3$ | 4-CN | H | >300 | Base | 2 |
| 21 | $CH_3$ | 3-$CF_3$ | H | 236 | Hydrochloride | 2 |
| 22 | $CH_3$ | 4-F | H | 255 | Hydrochloride | 2 |

I claim:

1. Process for the treatment of cardiac insufficiency in a warm-blooded organism, which comprises administering to the warm-blooded organism a compound or a physiologically tolerated acid addition salt or an N-oxide thereof, in an amount which has a positive inotropic effect said compound being a substituted phenyl-2-(1H)-pyrimidinone of the formula I

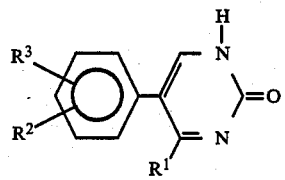

in which $R^1$ denotes an alkyl group having 1 to 4 carbon atoms, and $R^2$ and $R^3$, which are identical or different each denote hydrogen, halogen, cyano, a trifluoromethyl group, a hydroxyl group or an alkoxy group having 1 to 4 carbon atoms, each alkyl moiety being straight-chain or branched.

2. A process for the treatment of cardiac insufficiency as provided in claim 1 wherein the administered compound is 5-(4-hydroxyphenyl)-4-methyl-2-(1H)-pyrimidinone hydrobromide.

3. A process for the treatment of cardiac insufficiency as provided in claim 1 wherein the administered compound is 5-(4-methoxyphenyl)-4-methyl-2-(1H)- pyrimidinone and 5-(4-chlorophenyl)-4-methyl-2-(1H)-pyrimidinone.

4. A process for the treatment of cardiac insufficiency as provided in claim 1 wherein the administered compound is 5-(3-hydroxyphenyl)-4-methyl-2-(1H)-pyrimidinone hydrobromide.

5. A process for the treatment of cardiac insufficiency as provided in claim 1 wherein the administered compound is 5-(3-methoxyphenyl)-4-methyl-2-(1H)-pyrimidinone, 5-(3-chlorophenyl)-4-methyl-2-(1H)-pyrimidinone, 5-(4-hydroxyphenyl)-4-methyl-2-(1H)-pyrimidinone hydrobromide.

* * * * *